United States Patent [19]

Perettie et al.

[11] 4,225,718
[45] Sep. 30, 1980

[54] PROCESS FOR RECOVERING 2,3,5,6-TETRACHLOROPYRIDINE

[75] Inventors: Donald J. Perettie; Norman L. Dean, both of Lake Jackson, Tex.

[73] Assignee: The Dow Chemical Company, Midland, Mich.

[21] Appl. No.: 14,385

[22] Filed: Feb. 22, 1979

Related U.S. Application Data

[63] Continuation-in-part of Ser. No. 909,610, May 25, 1978, abandoned, which is a continuation of Ser. No. 806,037, Jun. 13, 1977, abandoned.

[51] Int. Cl.$^2$ ............................................. C07D 213/04
[52] U.S. Cl. ................................................. 546/345
[58] Field of Search ......................................... 546/345

[56] References Cited

U.S. PATENT DOCUMENTS

| 3,370,062 | 2/1965 | Corran | 546/345 |
| 3,732,230 | 5/1973 | Brewer et al. | 546/345 |

Primary Examiner—Alan L. Rotman
Attorney, Agent, or Firm—S. Preston Jones; Ronald G. Brookens; L. Wayne White

[57] ABSTRACT

Substantially pure 2,3,5,6-tetrachloropyridine is recovered from a mixture of chlorinated pyridines containing initially 2,3,5,6-tetrachloropyridine and other chlorinated pyridines in an improved process which comprises (a) reacting by contacting a first mixture of chlorinated pyridines with chlorine in the presence of a strong Lewis acid catalyst to thereby obtain a second mixture consisting essentially of 2,3,5,6-tetrachloropyridine and pentachloropyridine, and (b) recovering the 2,3,5,6-tetrachloropyridine from said second mixture. The reaction is normally conducted at a temperature of from about 150° C. to about 300° C. by pressurizing chlorine into a molten mixture of the chlorinated pyridines and maintaining such conditions until substantially all of the isomers have been converted to the symmetrical tetrachloropyridine or pentachloropyridine.

7 Claims, No Drawings

PROCESS FOR RECOVERING 2,3,5,6-TETRACHLOROPYRIDINE

RELATION TO PRIOR APPLICATIONS

This application is a continuation-in-part of application Ser. No. 909,610, filed May 25, 1978 now abandoned, which in turn is a continuation of application Ser. No. 806,037 filed June 13, 1977, now abandoned.

BACKGROUND OF THE INVENTION

This invention is directed to a novel process for recovering substantially pure 2,3,5,6-tetrachloropyridine from mixtures of chlorinated pyridines. Highly chlorinated pyridine compounds, such as 2,3,5,6-tetrachloropyridine, are known to be useful as pesticides or as intermediates for the preparation of other compounds having pesticidal properties. The various processes used to prepare chlorinated pyridines and especially 2,3,5,6-tetrachloropyridine have generally resulted in producing product mixes containing many chlorinated compounds including 2,3,4,5- and 2,3,4,6-tetrachloropyridine, the two position isomers of the desired 2,3,5,6-tetrachloropyridine. It has been particularly difficult to separate 2,3,5,6-tetrachloropyridine from its two position isomers by conventional economical techniques such as distillation since the boiling points of these three materials are so close. It has therefore been necessary to resort to more costly, difficult and time-consuming procedures of selective crystallization and multistage and/or multiplate distillation.

It has been discovered that both 2,3,4,5- and 2,3,4,6-tetrachloropyridine are converted to pentachloropyridine at a much more rapid rate than 2,3,5,6-tetrachloropyridine when they are chlorinated in the presence of a Lewis acid catalyst. Because of this difference in reaction rates, both 2,3,4,5- and 2,3,4,6-tetrachloropyridine can be substantially converted to pentachloropyridine prior to substantial conversion of any 2,3,5,6-tetrachloropyridine which might be in admixture with the above isomers. The separation of 2,3,5,6-tetrachloropyridine from pentachloropyridine is a rather easy procedure.

SUMMARY OF THE INVENTION

A process has now been discovered that substantially pure 2,3,5,6-tetrachloropyridine can be recovered from a mixture containing initially 2,3,5,6-tetrachloropyridine, pentachloropyridine and at least one of 2,3,4,5-tetrachloropyridine and 2,3,4,6-tetrachloropyridine and no more than minor amounts, if any, of monochloropyridines, 3,5-dichloropyridine, 2,3,5-trichloropyridine and 2,3,6-trichloropyridine and no other chloropyridine compounds. The novel process comprises the steps of (a) reacting by contacting a first mixture of chlorinated pyridines with chlorine in the presence of a Lewis acid catalyst to thereby obtain a second mixture of chlorinated pyridines consisting essentially of 2,3,5,6-tetrachloropyridine and pentachloropyridine, and (b) recovering the 2,3,5,6-tetrachloropyridine from said second mixture. The first mixture of chlorinated pyridines consist essentially of 2,3,5,6-tetrachloropyridine, pentachloropyridine and at least one of 2,3,4,5-tetrachloropyridine and 2,3,4,6-tetrachloropyridine and no more than minor amounts, if any, of monochloropyridines, 3,5-dichloropyridine, 2,3,5-trichloropyridine and 2,3,6-trichloropyridine and no other chloropyridine compounds.

There are several commercially significant advantages of the instant process over prior art procedures. First, the instant process results in a mixture consisting essentially of symmetrical tetrachloropyridine and pentachloropyridine; which is easily separated by conventional techniques (e.g., distillation). Second, pentachloropyridine is known to be a starting material for use in reductive reactions leading to tetrachloropyridines and the pentachloropyridine produced in the instant process can be recovered and recycled to generate additional symmetrical tetrachloropyridine. Third, the instant process is a straightforward facile process which obviates the need of expensive, sophisticated distillation apparatus or selective crystallization apparatus to recover symmetrical tetrachloropyridine from a mixture of close boiling position isomers of tetrachloropyridine or a mixture of polychlorinated pyridines. Significant capital savings as well as reduced operating expenditures are thus substantially achieved. These and other advantages will be readily apparent to those skilled in the art of manufacturing symmetrical tetrachloropyridine.

DETAILED DESCRIPTION OF THE INVENTION

The reactants in this process are well-known. A mixture of chlorinated pyridines which contains 2,3,5,6-tetrachloropyridine can be used in the instant process. Such mixtures can contain mono-, 3,5-di-, tri-, tetra- and/or pentachloropyridine along with the symmetrical tetrachloropyridine. Normally, commercial routes of producing symmetrical tetrachloropyridine result in a mixture of tri-, tetra- and pentachloropyridines. All of these mixtures normally melt at elevated temperatures (e.g., 90° C.–125° C.) and the molten mixture is used as the reaction medium in the present process.

Chlorine is a gas which is normally soluble or otherwise entrained in the molten chloropyridine mixtures. This solubility is enhanced by pressure.

The catalysts in the instant process are strong Lewis acids. Examples of Lewis acids which can be employed in the present process include, o-phosphoric acid, boron trifluoride, aluminum chloride, aluminum oxychloride, chromium trichloride, ferric chloride, ruthenium chloride, and the corresponding bromides, aluminum oxide, ferric oxide, ferric acetylacetonate, and the like. The catalyst, which is normally a solid can be employed as such (unsupported) or the catalyst can be supported on a carrier. Representative carriers include, molecular sieves, gamma alumina, silica, silica gel, silica-alumina, graphite and the like. It has been observed that Lewis acids in which the metal or cationic portion of the compound has an oxidation state of plus 3 or more (usually +3 or +5) as the predominant configuration (e.g. Fe +3) are normally catalysts in the instant process. Such compounds are considered by those skilled in the art to be strong Lewis acids.

The preferred compounds are Lewis acids which are covalent metal halides and the most preferred catalysts are ferric chloride and aluminum chloride. The covalent metal halides can be used per se (which is the desired embodiment) or they can be generated in situ by adding the metal to the reaction mixture. For example, iron or aluminum can be added to the reaction mixture and ferric chloride and aluminum chloride will be generated in situ.

The catalysts are used in the instant process in small but catalytic amounts. Normally this will include amounts of up to about 10 weight percent, based on the weight of the chloropyridine reactant mixture. Preferably, however, the catalyst is included in amounts of from only about 0.05 to about 0.5 weight percent. The catalysts are quite effective and generally the lesser amount is satisfactory and facilitates removal of the catalyst at the end of the reaction.

The reaction may be conducted by contacting the chloropyridine mixtures with chlorine in the presence of the catalyst by a slurry technique or by contacting the mixture with the catalyst over a static bed or a fluidized bed of the catalyst. The process may be conducted in a batchwise manner, a continuous manner or a cyclic batch manner in which the pentachloropyridine and symmetrical tetrachloropyridine are removed leaving the catalyst in a distillation residue or in a quantity of the reaction mixture in the reaction vessel and fresh reactants then merely introduced into the reaction vessel. In this manner, the catalyst is recovered and reused. The reaction is conducted at elevated temperatures normally above the melting point of the chloropyridine mixture. Desirable rates of reaction have been achieved at temperatures of from about 150° C. to about 300° C. although somewhat higher or lower temperatures could be used, if desired. Preferred rates of reaction have been observed at temperatures of from about 200° C. to about 250° C.

The reaction can be conducted at atmospheric or superatmospheric pressure (e.g., 15-75 psig or higher) but superatmospheric pressures are normally desired. As noted before, chlorine is a gas and the solubility of chlorine in the chloropyridine mixtures is enhanced by use of superatmospheric pressures. This superatmospheric pressure may be provided with chlorine or an inert gas (e.g., nitrogen or HCl) but is normally provided by chlorine gas.

The instant process may be conducted in the presence of an inert solvent, if desired, but is preferably conducted neat. Suitable inert solvents include chlorinated hydrocarbons such as for example methyl chloroform, carbon tetrachloride, and the like.

The following examples will further illustrate the invention.

EXPERIMENTAL

The following experiments were conducted in a glass reaction vessel at atmospheric pressure and in a high pressure stainless steel autoclave at elevated pressures. The analysis of the reaction mixture and end products was accomplished by vapor phase chromatography.

EXAMPLES 1-5

A mixture of chlorinated pyridines was charged to an externally heated glass reactor vessel equipped with a mechanical stirrer, reflux condenser and a glass sparger and the mixture heated until molten. The mixture of chloropyridines included some or all of the following compounds in various amounts: 3,5-Dichloropyridine, 2,3,5-trichloropyridine, 2,3,6-trichloropyridine, pentachloropyridine and the three-position isomers of tetrachloropyridine. Ferric chloride was added to this molten mixture with stirring. The molten mixture was then heated to approximately 200° C. and chlorine was sparged into the reaction mixture. The course of the reaction was followed by taking analytical samples of the reaction mixture from time to time and following the disappearance of the undesirable isomers in the gas chromatograph. The data from these examples (runs) are summarized in Table I below.

TABLE I

| Run No. | Catalyst Type | Catalyst Wt % | Run Time (Hrs) | Component Analysis Feed (Wt %) | | | | |
|---|---|---|---|---|---|---|---|---|
| | | | | 3,5 Di | 2,3,5 Tri | 2,3,6 Tri | Tetras | Penta |
| 1 | None | — | 4 | — | — | — | 73.37 | 25.36 |
| 2 | FeCl$_3$ | 0.05 | 6 | — | — | — | 73.43 | 25.21 |
| 3 | FeCl$_3$ | 0.50 | 3 | — | — | — | 73.71 | 24.61 |
| 4 | FeCl$_3$ | 3.21 | 2 | — | — | — | 73.22 | 25.66 |
| 5 | FeCl$_3$ | 2.94 | 5 | 0.096 | 2.834 | 0.662 | 67.23 | 23.19 |

| Run No. | Catalyst Type | % Conversion | | | | | |
|---|---|---|---|---|---|---|---|
| | | 3,5 Di | 2,3,5 Tri | 2,3,6 Tri | 2,3,4,5 | 2,3,4,6 | 2,3,5,6 |
| 1 | None | — | — | — | 6.04 | 7.87 | 5.22 |
| 2 | FeCl$_3$ | — | — | — | 17.47 | 56.59 | 4.37 |
| 3 | FeCl$_3$ | — | — | — | 12.66 | 100 | 7.06 |
| 4 | FeCl$_3$ | — | — | — | 65.81 | 100 | 13.49 |
| 5[a] | FeCl$_3$ | 100 | 77.98 | 100 | −143 | 97.4 | −0.1 |

[a] In this Run, 3,5-dichloropyridine was converted to 2,3,5-trichloropyridine which was converted to both 2,3,4,5- and 2,3,5,6-tetrachloropyridine and pentachloropyridine. 2,3,6-Trichloropyridine was converted to 2,3,5,6-tetrachloropyridine and pentachloropyridine. Additional reaction time would increase pentachloropyridine production and give substantially complete chlorination of 2,3,5-trichloropyridine, 2,3,4,5- and 2,3,4,6-tetrachloropyridine.

| Run No. | Catalyst Type | Tetrachloropyridine Isomer Distribution in Percent of Total Tetra's | | | | | |
|---|---|---|---|---|---|---|---|
| | | Initial | | | Final | | |
| | | 2,3,4,5 | 2,3,4,6 | 2,3,5,6 | 2,3,4,5 | 2,3,4,6 | 2,3,5,6 |
| 1 | None | 0.126 | 2.673 | 97.20 | 0.125 | 2.600 | 97.27 |
| 2 | FeCl$_3$ | 0.121 | 2.664 | 97.21 | 0.106 | 1.228 | 98.67 |
| 3 | FeCl$_3$ | 0.115 | 2.621 | 97.26 | 0.111 | — | 98.87 |
| 4 | FeCl$_3$ | 0.123 | 2.699 | 97.18 | 0.050 | — | 99.95 |
| 5 | FeCl$_3$ | 0.140 | 2.86 | 97.00 | 0.350 | 0.076 | 99.57 |

The negative numbers under "percent conversion" in Table I means that that particular isomer was being produced during the course of the reaction. The positive numbers, on the other hand, indicate that that particular isomer was being consumed during the course of the reaction and leading to reduced amounts of that material in the final product. The reader will note the very desirable ratio of symmetrical tetrachloropyridine to the other position isomers thereof in the final product. No di- or trichloropyridines were observed in the final product (except Run 5 as noted above). Final product thus consisted essentially of pentachloropyridine and symmetrical tetrachloropyridine. This mixture was resolved into pentachloropyridine and symmetrical tetrachloropyridine (along with any minor amounts of tetrachloropyridine position isomers) by distillation under reduced pressure.

The dashes in Table I means that none of that particular isomer was present in either the feed or the final reaction product.

EXAMPLES 6-31

In this series of experiments, a mixture of tetra- and pentachloropyridines was charged to a high pressure stainless steel autoclave, the reaction mixture melted, and the catalyst indicated in Table II added. The autoclave was subsequently sealed, heated to reaction temperature, and pressurized with a pad of chlorine entering through a top valve. Once pressurized, chlorine gas was then continuously sparged through the reaction mixture with stirring and analytical samples taken during the course of the reaction. The data from these experiments are summarized in Table II.

TABLE II

| | REACTANT CONDITIONS | | RUN CONDITIONS | | | % TETRACHLOROPHYRIDINE ISOMER DISTRIBUTION OF TOTAL TETRA'S IN FEED | | |
|---|---|---|---|---|---|---|---|---|
| Exp. | Catalyst Type | Wt. % of Catalyst to Total Tetra's | Time Hrs. | Temp. °C. | Press. psig | 2, 3, 4, 5 | 2, 3, 4, 6 | 2, 3, 5, 6 |
| 1 | $FeCl_3$ | 0.05 | 1.75 | 206 | 55 | 0.136 | 2.676 | 97.19 |
| 2 | $FeCl_3$ | 0.50 | 1.75 | 202 | 51 | 0.127 | 2.630 | 97.243 |
| 3 | $FeCl_3$ | 5.03 | 0.75 | 201 | 49 | 0.045 | 1.68 | 98.28 |
| 4 | $FeCl_3$ | 0.50 | 1.25 | 242 | 25 | 0.027 | 1.794 | 98.18 |
| 5 | $FeCl_3$ | 0.50 | 3.0 | 241 | 52 | 0.418 | 20.21 | 79.37 |
| 6 | $FeCl_3$ | 0.50 | 0.75 | 238 | 74 | 0.037 | 1.768 | 98.11 |
| 7 | $FeCl_3$ | 0.5 | 4.5 | 160 | 51 | 0.061 | 2.13 | 97.81 |
| 8 | $FeCl_3$ | 0.50 | 2.5 | 180 | 53 | 0.033 | 2.40 | 97.60 |
| 9 | $FeCl_3$ | 0.50 | 1.75 | 212 | 50 | 0.069 | 1.93 | 97.99 |
| 10 | $FeCl_3$ | 0.50 | 3.0 | 241 | 52 | 0.418 | 20.21 | 79.37 |
| 11 | $FeCl_3$ | 0.05 | 7.0 | 180 | 49 | 0.030 | 2.06 | 97.91 |
| 12 | $FeCl_3$ | 0.05 | 7.0 | 200 | 25 | 0.093 | 4.904 | 95.00 |
| 13 | $FeCl_3$ | 0.05 | 4.0 | 241 | 52 | 0.418 | 20.21 | 79.37 |
| 14 | $AlCl_3$ | 0.43 | 1.50 | 220 | 50 | 0.070 | 2.01 | 97.92 |
| 15 | $Al_2O_3$ | 1.43 | 2.50 | 240 | 51 | 0.030 | 1.745 | 98.22 |
| 16 | $Fe_2O_3$ | 5.02 | 3.0 | 243 | 54 | 0.034 | 1.814 | 98.15 |
| 17 | *Fe | 0.49 | 3.0 | 243 | 51 | 0.180 | 12.69 | 87.13 |
| 18 | $SbCl_5$ | 0.90 | 1.25 | 222 | 50 | 0.069 | 1.930 | 97.99 |
| 19 | $ZnCl_2$ | 0.42 | 4.0 | 207 | 51 | 0.127 | 2.630 | 97.24 |
| 20 | None | — | 4.0 | 203 | 50 | 0.136 | 2.676 | 97.19 |
| 21 | AlOCl | 0.987 | 2 | 220 | 25 | 0.088 | 8.948 | 90.96 |
| 22 | $AlCl_3$on 13 X molecular sieve | 0.421 | 1 | 220 | 25 | 0.141 | 9.634 | 90.23 |
| 23 | 9.9% $AlCl_3$on Silica gel | 0.610 | 2 | 220 | 25 | 0.098 | 9.421 | 90.48 |
| 24 | $AlCl_3$on α alumina | 0.109 | 2 | 220 | 25 | 0.129 | 8.695 | 91.16 |
| 25 | 22.9% $AlCl_3$on Graphite | 1.130 | 4 | 220 | 25 | 0.067 | 6.658 | 93.28 |
| 26 | Filtrol Grade 13 Clay (a) | 2.050 | 2 | 220 | 25 | 0.150 | 9.615 | 90.24 |
| 27 | Nafion ® Powder 501 (b) | 7.843 | 4 | 219 | 25 | 0.120 | 9.553 | 90.34 |
| 28 | SK-500 Molecular Seive (c) | 7.843 | 5 | 220 | 25 | 0.112 | 9.616 | 90.27 |
| 29 | $H_3PO_4$ (solid) | 8.07 | 8 | 220 | 25 | 0.115 | 8.330 | 91.55 |
| 30 | Filtrol Grade 62 Clay (a) calcined | 7.843 | 5 | 220 | 25 | 0.210 | 9.537 | 90.24 |
| 31 | Filtrol Grade 62 Clay (a) uncalcined | 8.667 | 9 | 220 | 25 | 0.231 | 8.952 | 90.82 |

*Steel Wool
(a) Filtrol grades 13 and 62 are proprietary materials of the Filtrol Coproation and are acid activated clays with high Lewis acid properties.
(b) Nafion ® 501 is a proprietary material of E.I. DuPont DeNemours & Company and is a perfluorosulfonic acid resin. This material is a commercial acid catalyst.
(c) SK-500 is a proprietary material of Union Carbide Corporation. The material is an acid catalyst and is a crystalline aluminoslicate derived from Type Y molecular sieve.

| | % TETRACHLOROPYRIDINE ISOMER DISTRIBUTION IN PRODUCT | | | % TETRACHLOROPYRIDINE ISOMER CONVERSION | | |
|---|---|---|---|---|---|---|
| Exp. | 2, 3, 4, 5 | 2, 3, 4, 6 | 2, 3, 5, 6 | 2, 3, 4, 5 | 2, 3, 4, 6 | 2, 3, 5, 6 |
| 1 | 0.082 | 0.706 | 99.21 | 40.71 | 74.13 | 0.0 |
| 2 | 0.093 | 0.0 | 99.91 | 30.38 | 100.0 | 2.32 |
| 3 | 0.047 | 0.0 | 99.95 | 5.14 | 100.0 | 7.63 |
| 4 | 0.015 | 0.0 | 99.99 | 51.62 | 100.0 | 10.11 |
| 5 | 0.375 | 0.028 | 99.60 | 37.35 | 99.90 | 11.55 |
| 6 | 0.031 | 0.0 | 99.97 | 21.31 | 100.0 | 2.93 |
| 7 | 0.047 | 0.27 | 99.68 | 16.67 | 86.28 | — |
| 8 | 0.050 | 0.020 | 99.93 | — | 99.16 | — |
| 9 | 0.058 | 0.0 | 99.94 | 20.08 | 100.0 | 3.03 |
| 10 | 0.375 | 0.028 | 99.60 | 37.35 | 99.90 | 11.5 |

TABLE II-continued

| | | | | | | |
|---|---|---|---|---|---|---|
| 11 | 0.04 | 0.195 | 99.76 | — | 90.76 | 0.74 |
| 12 | 0.086 | 0.027 | 99.89 | 10.51 | 99.47 | — |
| 13 | 0.261 | 0.010 | 99.73 | 57.87 | 99.96 | 14.39 |
| 14 | 0.062 | 0.0 | 99.94 | 17.11 | 100.0 | 4.35 |
| 15 | 0.019 | 0.063 | 99.91 | 37.63 | 98.34 | 0.16 |
| 16 | 0.017 | — | 99.98 | 72.38 | 100.0 | 42.72 |
| 17 | 0.140 | — | 98.85 | 53.71 | 97.67 | 13.52 |
| 18 | 0.060 | 0.899 | 99.04 | 16.01 | 55.01 | 2.38 |
| 19 | 0.109 | 3.166 | 96.78 | 13.08 | −19.37 | −0.8 |
| 20 | 0.107 | 2.896 | 96.99 | 22.22 | −6.99 | 1.34 |
| 21 | 0.177 | 0.055 | 99.75 | −75.4 | 99.5 | 4.33 |
| 22 | 0.148 | 0.118 | 99.73 | 10.42 | 98.95 | 5.65 |
| 23 | 0.154 | 0.011 | 99.84 | −34.7 | 99.9 | 5.40 |
| 24 | 0.204 | 0.059 | 99.74 | −42.1 | 99.4 | 1.74 |
| 25 | 0.155 | 0.118 | 99.73 | −122.1 | 98.30 | −2.64 |
| 26 | 0.165 | 0.182 | 99.65 | 5.84 | 98.38 | 5.46 |
| 27 | 0.144 | 0.096 | 99.76 | −25.74 | 99.10 | 1.70 |
| 28 | 0.127 | 0.70 | 99.75 | 1.73 | 93.69 | 4.24 |
| 29 | 0.148 | 0.218 | 99.63 | −15.3 | 97.7 | 2.47 |
| 30 | 0.233 | 0.005 | 99.76 | 2.34 | 97.85 | 2.695 |
| 31 | 0.232 | 0.076 | 99.69 | 5.88 | 99.20 | −2.86 |

The data in Table II can be viewed in sections: Experiments 1–3 show the effect of catalyst concentration; experiments 4–6 show the effect of pressure on the reaction; experiments 7–13 show the effect of temperature on the reaction; experiments 14–31 show the effect of various catalysts in addition to ferric chloride; and experiments 19 and 20 also show the effect of a weak Lewis acid (i.e., zinc chloride) or no catalyst at all.

The negative numbers under "percent conversion" in Table II means that that particular isomer was being produced during the course of the reaction while the positive numbers, on the other hand, indicate that that particular isomer was being consumed during the course of the reaction and leading to reduced amounts of that material in the final product. In the above Runs, the small amount of 3,5-dichloropyridine present (not listed in the feed makeup) was converted to 2,3,5-trichloropyridine which in turn was converted to 2,3,4,5-, and 2,3,5,6-tetrachloropyridine and pentachloropyridine. The 2,3,6-trichloropyridine (also not listed as part of the feed makeup) was converted to 2,3,5,6-tetrachloropyridine and pentachloropyridine. Additional reaction time would increase pentachloropyridine production and give substantially complete chlorination of 2,3,5-trichloropyridine, 2,3,4,5- and 2,3,4,6-tetrachloropyridine.

The dashes in Table II means that none of that particular isomer was present in the final reaction product.

These reaction mixtures were likewise resolved into pentachloropyridine and symmetrical tetrachloropyridine using distillative techniques.

The above examples show that the instant process is very effective in resolving a complex mixture of chlorinated pyridines into a mixture consisting essentially of pentachloropyridine and symmetrical tetrachloropyridine which are easily resolved by conventional techniques. Various catalysts have been used in these examples and various other process parameters have been illustrated. Other catalysts and/or process parameters can be varied according to the above teaching.

What is claimed is:

1. A process for recovering 2,3,5,6-tetrachloropyridine from a first mixture containing initially 2,3,5,6-tetrachloropyridine, pentachloropyridine and at least one of 2,3,4,5-tetrachloropyridine and 2,3,4,6-tetrachloropyridine and no more than minor amounts, if any, of monochloropyridines, 3,5-dichloropyridine, 2,3,5-trichloropyridine and 2,3,6-trichloropyridine and no other chloropyridine compounds which comprises the steps of (a) reacting by contacting said first mixture of chlorinated pyridines at a temperature of from about 150° C. to about 300° C., in liquid phase, under atmospheric or superatmospheric pressure, with chlorine, in the presence of a small but catalytic amount of a Lewis acid catalyst whereby most of the 2,3,5,6-tetrachloropyridine does not undergo further chlorination while most if not all of the 2,3,4,5- and/or 2,3,4,6-tetrachloropyridine undergoes further chlorination to pentachloropyridine, to thereby obtain a second mixture of chlorinated pyridines consisting essentially of 2,3,5,6-tetrachloropyridine and pentachloropyridine, and (b) distilling said second mixture to recover the 2,3,5,6-tetrachloropyridine therefrom.

2. The process defined in claim 1 wherein said Lewis acid is a covalent metal chloride.

3. The process defined in claim 2 wherein said Lewis acid is ferric chloride or aluminum chloride.

4. The process defined in claim 3 wherein said Lewis acid is present in amount of up to about 10 weight percent, based on the weight of the first mixture of chlorinated pyridines.

5. The process defined in claim 4 wherein said Lewis acid is present in amount of from about 0.05 to about 0.5 weight percent.

6. The process defined in claim 5 wherein said reaction temperature is from about 200° to about 250° C.

7. The process defined in claim 6 wherein the reaction of Step (a) is conducted neat.

* * * * *